(12) United States Patent
Hansson et al.

(10) Patent No.: US 8,741,348 B2
(45) Date of Patent: Jun. 3, 2014

(54) PHYSICALLY AND CHEMICALLY STABLE NICOTINE-CONTAINING PARTICULATE MATERIAL

(75) Inventors: Henri Hansson, Helsingborg (SE); Arne Kristensen, Helsingborg (SE)

(73) Assignee: Niconovum AB, Helsingborg (SE)

( * ) Notice: Subject to any disclaimer, the term of this patent is extended or adjusted under 35 U.S.C. 154(b) by 1940 days.

(21) Appl. No.: 10/742,580

(22) Filed: Dec. 19, 2003

(65) Prior Publication Data

US 2004/0191322 A1 Sep. 30, 2004

Related U.S. Application Data

(60) Provisional application No. 60/514,050, filed on Oct. 24, 2003.

(30) Foreign Application Priority Data

Dec. 20, 2002 (DK) .................................. 2002 01984

(51) Int. Cl.
*A61K 9/14* (2006.01)

(52) U.S. Cl.
USPC .......................................... 424/489; 424/494

(58) Field of Classification Search
USPC .......................... 424/439, 441, 489, 499, 500
See application file for complete search history.

(56) References Cited

U.S. PATENT DOCUMENTS

| | | |
|---|---|---|
| 865,026 A | 9/1907 | Ellis |
| 940,521 A | 11/1909 | Endicott |
| 3,777,029 A | 12/1973 | Magid |
| 3,877,468 A | 4/1975 | Lichtneckert et al. |
| 4,317,837 A | 3/1982 | Kehoe et al. |
| 4,579,858 A | 4/1986 | Ferno et al. |
| 4,593,572 A | 6/1986 | Linley, Jr. |
| 4,655,231 A | 4/1987 | Ray et al. |
| 4,674,491 A | 6/1987 | Brugger et al. |
| 4,696,315 A | 9/1987 | Summers |
| 4,806,356 A | 2/1989 | Shaw |
| 4,817,640 A | 4/1989 | Summers |
| 4,835,162 A | 5/1989 | Abood |
| 4,907,605 A | 3/1990 | Ray et al. |
| 4,945,929 A | 8/1990 | Egilmex et al. |
| 4,967,733 A | 11/1990 | Rousseau et al. |
| 4,967,773 A | 11/1990 | Shaw |
| 4,971,079 A | 11/1990 | Talapin et al. |
| 5,069,904 A | 12/1991 | Masterson et al. |
| 5,077,104 A | 12/1991 | Hunt et al. |
| 5,135,753 A | 8/1992 | Baker et al. |
| 5,167,242 A | 12/1992 | Turner et al. |
| 5,268,209 A | 12/1993 | Hunt et al. |
| 5,284,163 A | 2/1994 | Knudsen et al. |
| 5,318,523 A | 6/1994 | Lu et al. |
| 5,326,570 A | 7/1994 | Rudnic et al. |
| 5,346,589 A | 9/1994 | Braunstein et al. |
| 5,488,962 A | 2/1996 | Perfetti et al. |
| 5,501,858 A | 3/1996 | Fuisz |
| 5,507,278 A | 4/1996 | Karell |
| 5,525,351 A | 6/1996 | Dam et al. |
| 5,543,424 A | 8/1996 | Carlsson et al. |
| 5,549,906 A | 8/1996 | Santus et al. |
| 5,573,774 A | 11/1996 | Keenan |
| 5,599,554 A | 2/1997 | Majeti |
| 5,643,905 A | 7/1997 | Moormann et al. |
| 5,654,003 A | 8/1997 | Fuisz et al. |
| 5,656,255 A | 8/1997 | Jones et al. |
| 5,692,493 A | 12/1997 | Weinstein et al. |
| 5,711,961 A | 1/1998 | Reiner et al. |
| 5,721,257 A * | 2/1998 | Baker et al. .................. 514/343 |
| 5,733,574 A | 3/1998 | Dam et al. |
| 5,810,018 A | 9/1998 | Monte |
| 5,935,604 A * | 8/1999 | Illum ............................ 424/501 |
| 5,939,100 A | 8/1999 | Albrechtsen et al. |
| 5,955,098 A | 9/1999 | Dugger, III |
| 6,024,981 A | 2/2000 | Khankari et al. |
| 6,083,531 A | 7/2000 | Humbert-Droz et al. |
| 6,110,495 A | 8/2000 | Dam et al. |
| 6,129,936 A | 10/2000 | Gustafsson et al. |
| 6,183,775 B1 | 2/2001 | Ventouras |
| 6,264,981 B1 | 7/2001 | Zhang et al. |
| 6,280,761 B1 | 8/2001 | Santus .......................... 424/435 |

(Continued)

FOREIGN PATENT DOCUMENTS

| | | |
|---|---|---|
| CN | 1079650 | 12/1993 |
| CN | 1089834 | 7/1994 |

(Continued)

OTHER PUBLICATIONS

Database WPI Week 198651, Derwent Publications Ltd., XP-002247927 (1986).

(Continued)

*Primary Examiner* — Michael G Hartley
*Assistant Examiner* — Micah-Paul Young
(74) *Attorney, Agent, or Firm* — Womble Carlyle Sandridge & Rice, LLP (57) ABSTRACT

A nicotine-containing particulate material for release of nicotine, the material comprising a combination of nicotine or a pharmaceutically acceptable salt, complex or solvate thereof and a microcrystalline cellulose. The particulate material is stable upon storage and releases nicotine relatively fast. The particulate material can be used in the manufacture of nicotine containing pharmaceutical composition, wherein the release of nicotine can be designed to be relatively fast so as to obtain a fast onset of action.

56 Claims, 2 Drawing Sheets

(56) References Cited

U.S. PATENT DOCUMENTS

| | | |
|---|---|---|
| 6,287,596 B1 | 9/2001 | Murakami et al. |
| 6,344,222 B1 | 2/2002 | Cherukuri et al. |
| 6,358,527 B1 | 3/2002 | Gilis et al. |
| 6,841,557 B2 | 1/2005 | Anderson et al. |
| 6,845,777 B2 | 1/2005 | Pera |
| 6,849,624 B2 | 2/2005 | Ballard et al. |
| 6,855,820 B2 | 2/2005 | Broom et al. |
| 6,858,624 B2 | 2/2005 | Hagen et al. |
| 6,861,434 B2 | 3/2005 | Stack |
| 6,872,405 B2 | 3/2005 | Takaishi et al. |
| 6,893,654 B2 | 5/2005 | Pinney et al. |
| 6,932,971 B2 | 8/2005 | Bachmann et al. |
| 6,958,143 B2 | 10/2005 | Choi et al. |
| 6,958,323 B2 | 10/2005 | Olivera et al. |
| 6,960,574 B2 | 11/2005 | Prokai |
| 6,982,089 B2 | 1/2006 | Tobinick |
| 2001/0016593 A1 | 8/2001 | Wilhelmsen |
| 2001/0029959 A1 | 10/2001 | Burgard et al. |
| 2002/0009523 A1 | 1/2002 | Gustaesson |
| 2002/0010198 A1 | 1/2002 | Jerussi et al. |
| 2002/0015687 A1 | 2/2002 | Bellamy et al. |
| 2003/0077297 A1 | 4/2003 | Chen et al. |
| 2003/0082109 A1 | 5/2003 | Gorenstein |
| 2003/0124191 A1 | 7/2003 | Besse et al. |
| 2003/0180360 A1 | 9/2003 | Am Ende et al. |
| 2003/0224048 A1 | 12/2003 | Walling |
| 2004/0013752 A1 | 1/2004 | Wolfson |
| 2005/0009813 A1 | 1/2005 | Moormann et al. |
| 2005/0009882 A1 | 1/2005 | Farr |
| 2005/0013856 A1 | 1/2005 | Trivedi et al. |
| 2005/0020641 A1 | 1/2005 | Sellers et al. |
| 2005/0042173 A1 | 2/2005 | Besse et al. |
| 2005/0058609 A1 | 3/2005 | Nazeri |
| 2005/0089524 A1 | 4/2005 | Sanderson et al. |
| 2005/0100513 A1 | 5/2005 | Watkins et al. |
| 2005/0107397 A1 | 5/2005 | Galambos et al. |
| 2005/0118272 A1 | 6/2005 | Besse et al. |
| 2005/0123502 A1 | 6/2005 | Chan et al. |
| 2005/0136047 A1 | 6/2005 | Ennifar et al. |
| 2005/0182063 A1 | 8/2005 | Yohannes |
| 2005/0197343 A1 | 9/2005 | Gmeiner et al. |
| 2005/0222270 A1 | 10/2005 | Olney et al. |
| 2005/0227998 A1 | 10/2005 | Voelker |
| 2005/0261289 A1 | 11/2005 | Flohr et al. |
| 2005/0277626 A1 | 12/2005 | Dinan et al. |
| 2005/0282823 A1 | 12/2005 | Breining et al. |
| 2006/0057207 A1 | 3/2006 | Ziegler et al. |
| 2006/0058328 A1 | 3/2006 | Bhatti et al. |
| 2006/0062835 A1 | 3/2006 | Weil |
| 2006/0084656 A1 | 4/2006 | Ziegler et al. |
| 2006/0171969 A1 | 8/2006 | Macelloni et al. |
| 2006/0252773 A1 | 11/2006 | Ceci |
| 2006/0276551 A1 | 12/2006 | Shytle et al. |

FOREIGN PATENT DOCUMENTS

| | | | |
|---|---|---|---|
| CN | 1383814 | 12/2002 | |
| CN | 1511550 | 7/2004 | |
| CN | 1557177 | 12/2004 | |
| DE | 2313996 | 10/1974 | |
| DE | 2608156 | 9/1976 | |
| DE | 2526702 | 12/1976 | |
| DE | 3241437 | 5/1984 | |
| DE | 4301782 | 8/1994 | |
| DE | 19639343 | 4/1998 | |
| DE | 29800300 | 4/1998 | |
| DE | 19943491 | 3/2001 | |
| EP | 205133 | 12/1986 | |
| EP | 215682 | 3/1987 | |
| EP | 0324794 | 7/1989 | |
| EP | B0324794 | 7/1989 | |
| EP | 377520 | 7/1990 | |
| EP | 472428 | 2/1992 | |
| EP | 485421 | 5/1992 | |
| EP | 500658 | 9/1992 | |
| EP | 506774 | 10/1992 | |
| EP | 506860 | 10/1992 | |
| EP | 0557129 | 8/1993 | |
| EP | 570327 | 11/1993 | |
| EP | 0619729 | 10/1994 | |
| EP | 680326 | 11/1995 | |
| EP | 0745380 | 12/1996 | |
| EP | 0839544 | 5/1998 | |
| EP | 850182 | 7/1998 | |
| EP | 0904055 | 3/1999 | |
| EP | 0916339 | 5/1999 | |
| EP | 1023069 | 8/2000 | |
| EP | 1044687 | 10/2000 | |
| EP | 1069900 | 1/2001 | |
| EP | 1136487 | 9/2001 | |
| EP | 02793665 | 12/2002 | |
| EP | 1267849 | 1/2003 | |
| EP | 1272218 | 1/2003 | |
| EP | 1448196 | 8/2004 | |
| EP | 1509227 | 3/2005 | |
| EP | 1534254 | 6/2005 | |
| EP | 1539149 | 6/2005 | |
| EP | 1539764 | 6/2005 | |
| EP | 1539765 | 6/2005 | |
| EP | 1551393 | 7/2005 | |
| EP | 1589952 | 11/2005 | |
| EP | 1624845 | 2/2006 | |
| EP | 1624895 | 2/2006 | |
| EP | 1634498 | 3/2006 | |
| EP | 1737431 | 1/2007 | |
| FR | 2147652 | 3/1973 | |
| FR | 2467604 | 4/1981 | |
| FR | 2 608 156 | 6/1988 | |
| FR | 2688400 | 9/1993 | |
| FR | 2698268 | 5/1994 | |
| FR | 2788982 | 8/2000 | |
| FR | 2792200 | 10/2000 | |
| GB | 1528391 | 10/1978 | |
| GB | 2030862 | 4/1980 | |
| GB | 2125699 | 3/1984 | |
| GB | 2 227 659 | 8/1990 | |
| GB | 2227659 | 8/1990 | |
| GB | 2227659 A * | 8/1990 | |
| GB | 2255892 | 11/1992 | |
| GB | 2289204 | 11/1995 | |
| GB | 2308992 | 7/1997 | |
| GB | 2393392 | 3/2004 | |
| JP | 52114010 | 9/1977 | |
| JP | 62228022 | 10/1987 | |
| JP | 1243945 | 9/1989 | |
| JP | 2072118 | 3/1990 | |
| JP | 2005082587 | 3/2005 | |
| JP | 2005103113 | 4/2005 | |
| JP | 2005320342 | 11/2005 | |
| KP | 2001078976 | 8/2001 | |
| RU | 2029474 | 2/1995 | |
| SU | 1232260 | 5/1986 | |
| SU | 1268141 | 11/1986 | |
| WO | WO-8302892 | 9/1983 | |
| WO | WO 91/01656 | 2/1991 | ............ A24B 15/16 |
| WO | WO-9101132 | 2/1991 | |
| WO | WO-9104757 | 4/1991 | |
| WO | WO-9106288 | 5/1991 | |
| WO | WO-9109599 | 7/1991 | |
| WO | WO 9109599 A1 * | 7/1991 | |
| WO | WO-9109731 | 7/1991 | |
| WO | WO-9312764 | 7/1993 | |
| WO | WO-9416708 | 8/1994 | |
| WO | WO-9503050 | 2/1995 | |
| WO | WO-9520411 | 8/1995 | |
| WO | WO-9702273 | 1/1997 | |
| WO | WO-9710162 | 3/1997 | |
| WO | WO 97/42941 | 11/1997 | |
| WO | WO-9915171 | 4/1999 | |
| WO | WO-9965550 | 12/1999 | |
| WO | WO-0019977 | 4/2000 | |
| WO | WO-0038686 | 7/2000 | |
| WO | WO-0044559 | 8/2000 | |

(56) References Cited

FOREIGN PATENT DOCUMENTS

| | | |
|---|---|---|
| WO | WO-0045795 | 8/2000 |
| WO | WO-0056281 | 9/2000 |
| WO | WO-0119401 | 3/2001 |
| WO | WO-01/30288 | 5/2001 |
| WO | WO-0130288 | 5/2001 |
| WO | WO-0137814 | 5/2001 |
| WO | WO-02076229 | 10/2002 |
| WO | WO-02102357 | 12/2002 |
| WO | WO-03013719 | 2/2003 |
| WO | WO-03045437 | 6/2003 |
| WO | WO-03053175 | 7/2003 |
| WO | WO-03055486 | 7/2003 |
| WO | WO-03061399 | 7/2003 |
| WO | WO-03077846 | 9/2003 |
| WO | WO-2004002446 | 1/2004 |
| WO | WO-2004004478 | 1/2004 |
| WO | WO-2004004479 | 1/2004 |
| WO | WO-2004004480 | 1/2004 |
| WO | WO-2004032644 | 4/2004 |
| WO | WO-2004056219 | 7/2004 |
| WO | WO-2004056363 | 7/2004 |
| WO | WO-2004064811 | 8/2004 |
| WO | WO-2004068964 | 8/2004 |
| WO | WO-2004068965 | 8/2004 |
| WO | WO-2004103372 | 12/2004 |
| WO | WO-2005007655 | 1/2005 |
| WO | WO-2005018348 | 3/2005 |
| WO | WO-2005023227 | 3/2005 |
| WO | WO-2005023781 | 3/2005 |
| WO | WO-2005028484 | 3/2005 |
| WO | WO-2005034968 | 4/2005 |
| WO | WO-2005040338 | 5/2005 |
| WO | WO-2005053691 | 6/2005 |
| WO | WO-2005066126 | 7/2005 |
| WO | WO-2006000232 | 1/2006 |
| WO | WO-2006008040 | 1/2006 |
| WO | WO-2006008041 | 1/2006 |
| WO | WO-2006028344 | 3/2006 |
| WO | WO-2006029349 | 3/2006 |
| WO | WO-2006037418 | 4/2006 |
| WO | WO-2006041769 | 4/2006 |
| WO | WO-2005084126 A3 | 11/2006 |
| WO | WO-2006115202 | 11/2006 |
| WO | WO-2006119884 | 11/2006 |
| WO | WO-2006138682 | 12/2006 |
| WO | WO-2007006117 | 1/2007 |

OTHER PUBLICATIONS

Database WPI Week 199143, Derwent Publications Ltd., XP-002247928 (1991).

Database WPI Week 199143, Derwent Publications Ltd., XP-002247929 (1991).

Gu Lihong et al "Preparation and pharmaceutical study of nicotine sustained release tablet",The Journal of Pharmaceutical Practice vol. 19, 2001 No. 4 pp. 288-289.

Quik M "Smoking, nicotine and Parkinson's disease", TRENDS in Neurosciences vol. 27, No. 9, Sep. 2004.

Sahakian, B.J. et al "Nicotine and Tetrahydroaminoacradine: Evidence for improved attention in patients and dementia of the Alzheimer Type", Dept of Experimental Psychology, University of Cambridge, UK, Drug Development Research 31:80-88, 1994.

Jenkusky, S.M. "Use of nicotine patches for schizophrenic patients", AM J. Psychiatry 150:12, Dec. 1993.

Thomas, G.A.O, et al "Transdermal Nicotine as Maintenance Therapy for Ulcerative Colitis", The New England Journal of Medicine, Apr. 13, 1995.

Axelsson et al., "The Anti-smoking Effect of chewing gum with nicotine of high and low bioavailability"; 3rd World Conference on Smoking and Health, New York, 1975.

Mihranyan et al., "Sorption of nicotine to cellulose powders", European Journal Pharmaceutical Sciences; 2004; 279-286; 22(4).

Mihranyan, "Engineering of Native Cellulose Structure for Pharmaceutical Applications, Influence of Cellulose Crystallinity Index, Surface Area and Pore Volume on Sorption Phenomena", ACTA Universitatis Upsaliensis Uppsala; 2005; 1-58.

Molander et al., "Pharmacokinetic investigation of a nicotine sublingual tablet", .Eur. J. Clin. Pharmacol. 2001; 813-9; vol. 56(11).

Morjaria et al., "In Vitro Release of Nicotine From Chewing Gum Formulations", Dissolution Technologies; May 2004; 12-15; vol. 11 (2).

Nasr, M.M., et al., (1998) In Vitro Study of Nicotine Release from Smokeless Tobacco, J. AOAC Int'l., V.81(3), 540-543.

Ullman's Encyclopedia of Industrial Chemistry, 5th Revised Ed. (1991), vol. A 19, Ed. Elvers, B., Hawkins, S. and Schulz, G.

http://www.fmc.com/—pages for Avicel products and MCC/Cellulose gel, Jan. 11, 2008.

http://en.wikipedia.org/wiki/Excipient, Jan. 11, 2008.

\* cited by examiner

PHYSICALLY AND CHEMICALLY STABLE NICOTINE-CONTAINING PARTICULATE MATERIAL

FIELD OF THE INVENTION

The present invention relates to a nicotine-containing particulate material comprising a microcrystalline cellulose into which nicotine or a pharmaceutically acceptable salt, complex or solvent thereof has been incorporated. The invention also relates to pharmaceutical compositions and for method for treating or preventing tobacco dependence. Parkinsons disease, ulcerative colitis, Alzheimers disease, schizophrenia and/or ADHD.

BACKGROUND OF THE INVENTION

The treatment with nicotine-containing products today produces either too small quantities of nicotine in plasma and/or plasma profiles with a too flat and/or slow peak. The desired plasma profile is one that has a faster uptake of nicotine than other marketed treatment products. To solve this problem nicotine in its base form is preferred. Nicotine in its base form is readily absorbed through the oral mucosa but is highly volatile and subject to oxidative degradation. The available nicotine salts are more stable compounds but are not as readily absorbed as the free base. In order to deal with the volatility and stability problems of the free base different techniques are possible.

In U.S. Pat. No. 5,939,100 nicotine in its base form is incorporated in degradable starch microspheres. The use of degradable starch microspheres with incorporated nicotine gives a 3-dimensional matrix releasing the nicotine in a rather sustained fashion depending on both binding properties, nicotine-starch matrix and the biological degradation profile of the microspheres.

In WO 91/09599 an inclusion complex is produced between nicotine and β-cyclodextrin. The release of nicotine from the produced complex was filled in a porous bag of synthetic material (type tea bag) and the plasma profile was measured with a peak nicotine concentration (8 ng/ml) after approx. 45 min. in humans. The release is highly dependent on the affinity of nicotine to β-cyclodextrin and considered rather slow.

In U.S. Pat. No. 4,967,773 synthetic silica is used together with nicotine. The rational for this is to ensure the stability in a lozenge where nicotine together with silica could be mixed with lactose. The manipulation is done due to the formulation of a product where incompatible constituents (nicotine and lactose) are desired.

In U.S. Pat. No. 4,907,605 nicotine is absorbed in different water insoluble materials, e.g. paper, cellulose acetate, polyethylene or polypropylene. The sorbed nicotine is to be released slowly in an oral environment.

In U.S. Pat. No. 6,264,981 solid solutions of different active principals with a dissolution agent are presented. Nicotine is mentioned as an active principal together with a list of other substances.

None of the above-mentioned documents has addressed the need for a truly rapid release and absorption of nicotine through the oral mucosa in combination with high physical and chemical stability. The need for a solid carrier is evident but the combination of sorbing nicotine in a solid matrix is not just a stability concern but equally, if not more important, are the release properties from the carrier.

DESCRIPTION OF THE INVENTION

The object of the present invention is to provide a physically and chemically stable nicotine-containing particulate material that can be designed to release nicotine relatively fast from the material in order to enable a rapid absorption after administration.

The inventors have surprisingly found that sorption of nicotine (e.g. in the form of a solution containing nicotine as a base) on a microcrystalline cellulose (MCC) results in physical and chemical stable dry particulate material with a very fast and complete release in vitro. The dissolution profiles of nicotine base from such a particulate material may typically be that about 90% of loaded nicotine released after 1 minute in 1 litre phosphate buffer, pH 7.4 maintained at 37° C. in a dissolution apparatus according to USP, paddle.

Thus, in one aspect the invention relates to a nicotine-containing particulate material for release of nicotine, the material comprising a combination of nicotine or a pharmaceutically acceptable salt, complex or solvate thereof and a microcrystalline cellulose, the particulate material—when tested in an in vitro dissolution test—releasing at least 90% w/w such as, .g. at least 95% w/w of the nicotine or the pharmaceutically acceptable salt, complex or solvat thereof within at the most about 30 min such as, e.g., at the most about 25 min, at the most about 20 min, at the most about 15 min, at the most about 10 min, at the most about 7.5 min. at the most about 5 min, at the most about 4 min, at the most about 3 min or at the most about 2 min.

More specifically, the invention relates to a particulate material for fast release of nicotine, the material—when tested in an in vitro dissolution test—releasing at least 90% w/w such as, e.g. at least 95% w/w of the nicotine or the pharmaceutically acceptable salt, complex or solvate thereof within at the most about 20 min such as, e.g. at the most about 15 min, at the most about 10 min, at the most about 7.5 min, at the most about 5 min, at the most about 4 min, at the most about 3 min, at the most about 2 min or at the most about 1 min.

The problem that goes parallel with tobacco smoking is its enormous implications on health. Today it is estimated that smoking related diseases cause some 3-4 million deaths annually. This grim consequence of tobacco smoking has lead many medical associations and health authorities to take very strong actions against the use of tobacco. More recently the World Health Organisation (WHO) has made the control of tobacco to a priority on par with the control of malaria.

Tobacco smoking can result in a dependence disorder. The WHO has in its International Classification of Disorders a diagnosis Tobacco Dependence. Others like the American Psychiatric Association labels the addiction Nicotine Dependence.

Nicotine is the world's second most used drug, after caffeine from coffee and tea. Even though tobacco smoking is decreasing in many developed countries today it is hard to see how the societies could get rid of the world's second most used drug. Societies are not even successful in protecting themselves against illegal drugs that have more profound psychotoxic effects. It is therefore most likely that when tobacco smoking will become more or less socially and legally outlawed there will be a need for discovering other forms of taking nicotine. Nicotine containing medications are currently the dominating treatments for tobacco dependence. There is also evidence of broader use of these medications like for smoking reduction and long term maintenance/substitution. However the products are not very acceptable to many smokers. Among other things they are too far from the cigarette in some major characteristics.

When smoke from a cigarette is inhaled, the nicotine reaches its targets in the brain in about 10 seconds. Most cigarettes normally contain 10-15 mg of nicotine. Most of that nicotine is not used by the smoker since a lot of the smoke is not inhaled and moreover a good amount of these 10-15 mg are left in the but. When the cigarette smokes itself and is forgotten in an ashtray then less nicotine is absorbed than when a smoker hungrily smokes a cigarette e.g. after a long meeting. On average something between 0.5-2 mg/cigarette is absorbed. The absorption is almost 100% of what is coming into the lower airways and the speed is very high.

The most widely used smoking cessation product, nicotine gum is marketed in two strengths, 2 and 4 mg, which is the actual content of nicotine. However the biological available dose from these gums are only about 1 and 2 mg, respectively. This is because it is difficult to completely empty the gum and some of the nicotine that is extracted from the gum cannot be absorbed into the circulatory system due to swallowing into the gastrointestinal tract where most of the nicotine is metabolised before entering the circulation. Moreover the speed by which the nicotine is absorbed is much slower than from the cigarette. This is an important factor since when individuals want to change their state of mind with psychoactive drugs the effects are strongly dependent on the speed by which the drug enters the brain.

Figure 1:
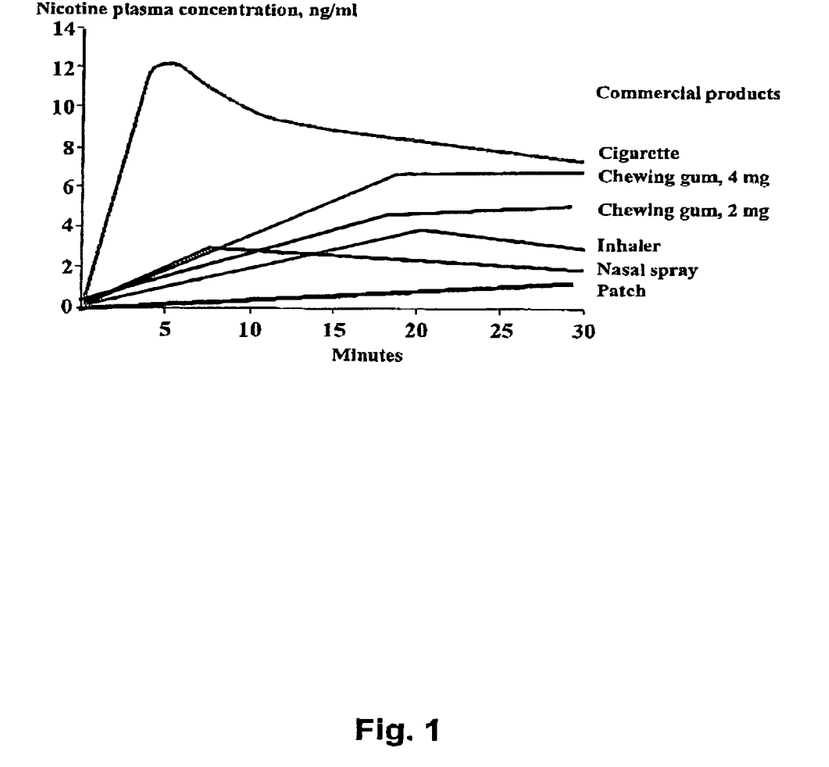
FIG. 1 shows the plasma concentration versus time profile of nicotine from commercially available products

Nicotine patches delivers from 15-21 mg nicotine (different brands have different doses). Most of the nicotine that is delivered through the skin is absorbed. For a smoker consuming 15-20 cigarettes a day one can assume a nicotine intake per day of 15-25 mg. If the smoking takes place during roughly a 16 hours waking period that means one to one and a half mg per hour. The nicotine patch gives close to one mg per hour. However one has to keep in mind that some smokers take in much more nicotine and that the pharmacokinetic profile of nicotine from a patch is relatively stable and does not allow for any discrete variations. With smoking there are peaks in nicotine concentration corresponding with each cigarette that may also be necessary for the experience of certain of the nicotine's effects. There are other products on the market today like Inhalers, a Sublingual tablet, a Lozenge and a Nasal spray. They all relatively well fall within the category of nicotine absorption that one can see from 2 and 4 mg gum, see FIG. 1 for a comparison with a cigarette. Many smokers, particularly those that ideally would like to continue with their smoking want nicotine stimulation that they easily can get from a cigarette but not at all from a nicotine patch. It is difficult but not entirely impossible to get nicotine stimulation from the other more acute delivery systems.

The dose and speed of absorption for producing a subjective effect (nicotine stimulation) may vary from individual to individual but it seems to be a rule that an increase in concentration of 5-10 ng/ml over 10 minutes is a requirement. The increase in concentration is time related so probably an increase of 3-5 ng/ml over 5 minutes is as good. This requirement to get a psychoactive effect is probably one of the most important characteristics in developing products that will be well accepted by consumers so they can rid themselves of the very high risk associated with cigarette smoking.

As mentioned above, a particulate material according to the present invention is chemically and physically stable. In the present context the term "stable" means that the material and/or the nicotine or the pharmaceutically acceptable salt, complex or solvate contained therein is chemically and/or physically stable for at least about 22 weeks such as, e.g., at least 14 weeks when stored open at a temperature of 40° C. and a relative humidity of 50%. It is especially of importance that nicotine or a pharmaceutically acceptable salt, complex or solvate thereof does not migrate out of the material as such a migration will lead to a marked loss in the content of nicotine in the material. Furthermore, as mentioned above, nicotine as a base is a volatile substance and, therefore, it is normally difficult to maintain a relatively constant concentration of the nicotine base in a composition comprising a mere admixture of nicotine and a pharmaceutically acceptable excipient. A particulate material according to the present invention is also physically stable. Thus, within a time period of 22 weeks or more no visible changes had been observed and the dissolution profile did not change.

It is contemplated that the microcrystalline cellulose is of utmost importance for the success of a particulate material according to the present invention.

However, other pharmaceutically acceptable excipients having the same behavior towards nicotine may of course also be of importance for the invention. Suitable microcrystalline celluloses are highly crystalline particulate cellulose containing crystallite aggregates obtained by removing amorphous (fibrous cellulose) regions of a purified cellulose source material by hydrolytic degradation, typically with a strong mineral acid such as hydrogen chloride. The acid hydrolysis process produces a microcrystalline cellulose of predominantly coarse particulate aggregate, typically having a mean size range of about 15 to 250 μm.

The microcrystalline cellulose (MCC) has a suitable porosity and/or bulk density, especially it has a very large surface area due to the porous structure of MCC. It is believed that nicotine after being contacted with MCC mainly is located in the porous structure of MCC, i.e. nicotine is sorbed to MCC most likely by adsorption. Accordingly, in an embodiment of the present invention at least part of the nicotine or the pharmaceutically acceptable salt, complex or solvate thereof is adsorbed to the microcrystalline cellulose in the particulate material.

MCM qualities suitable for the purpose of the present invention include but are not limited to any of commercial pharmaceutically accepted qualities of e.g. Avicele® such as, e.g., the grades PH-100, PH-102, PH-103, PH-105, PH-112, PH-113, PH-200, PH-300, PH-302, Vivacel® such as, e.g., grades 101, 102, 12 or 20, Emcocel® such as, e.g., the grades 50M or 90M.

Other crystalline celluloses are also contemplated to be suitable for use according to the invention. Without being bound to any theory, it is contemplated that due to its size and amphiphilic character, nicotine is entrapped and/or weekly bonded inside the void volume of the cellulose cells by means of hydrogen bonding or by Van deer Waals attraction.

To obtain a particulate material according to the present invention, the nicotine is dissolved in a hydrophilic solvent, i.e. water or alcohol or mixtures thereof, and, according to the above-mentioned theory it is contemplated that by means of capillary forces the nicotine is introduced into the voids of the crystalline cellulose. After the removal of the solvent nicotine is retained inside said voids until a suitable solvent again enters the voids and releases the nicotine into said solvent.

In the present context the term "nicotine" encompasses nicotine or a nicotine derivative in any form such as, e.g., physical form like amorphous, crystalline, polymorphous etc. or chemical form like isomers and enantiomers etc as well as any pharmaceutically acceptable salt, complex or solvate thereof. Nicotine may be selected from nicotine base, nicotine hydrochloride, nicotine dihydrochloride, nicotine monotartrate, nicotine bitartrate, nicotine sulfate, nicotine zinc chloride such as nicotine zinc chloride monohydrate and nicotine salicylate.

In a particulate material according to the present invention the concentration of nicotine or the pharmaceutically acceptable salt, complex or solvate thereof in the particulate material is at the most about 20% w/w such as, e.g., at the most about 15% w/w, at the most about 12.5% w/w, at the most about 10% w/w, at the most about 9.5% w/w, at the most about 9% w/w, at the most about 8.5% w/w or at the most about 8% w/w, and the concentration being calculated as the nicotine base.

In a specific embodiment, a particulate material according to the present invention has a concentration of nicotine or the pharmaceutically acceptable salt, complex or solvate thereof in the particulate material is at the most about 7.5% w/w such as, e.g., at the most about 7% w/w, at the most about 6.5% w/w, at the most about 6% w/w, at the most about 5.5% w/w, at the most about 5% w/w, at the most about 4.5% w/w, at the most about 4% w/w, at the most about 3% w/w, at the most about 2% w/w or at the most about 1% w/w, and the concentration being calculated as the nicotine base.

To this end, the present inventors have found that in order to obtain a relatively fast release the nicotine should typically be used in its base form. Moreover, the inventors have documented that if nicotine base is sorbed on MCC in concentrations of 0.1-8% (w/w) then a rapid absorption of nicotine in vivo takes place. Moreover, pH at the absorption site may influence the absorption rate and the inventors have found that at a pH≥7 suitable results have been obtained with respect to a rapid absorption. It seems as the absorption is decreased when the pH is lowered. However, such a decreased absorption rate may also be of therapeutic relevance and embodiments of the present invention relate especially to particulate material that releases nicotine or a pharmaceutically acceptable salt, complex or solvate thereof in a manner that results in a maximum concentration after 10-30 min after administration.

In order to obtain a suitable effect, a particulate material according to the present invention is a material, which—when administered to at least one healthy subject in the form of a chewing gum containing a particulate material containing 4 mg nicotine or an equivalent amount of a pharmaceutically acceptable salt, complex or solvate thereof—results in a plasma concentration of at least about 5 ng/ml such as, e.g., about 6 ng/ml or more, about 7 ng/ml or more, about 8 ng/ml or more, about 9 ng/ml or more or about 10 ng/ml or more of nicotine within at the most about 30 min such as, e.g. within at the most about 25 min, within at the most about 20 min, within at the most about 15 min or within at the most about 10 after administration.

In certain cases a very fast onset of action is desired and the nicotine contained in a particulate material or a composition according to the invention must be released relatively fast. In such specific embodiments a particulate material according to the present invention is a material, which—when administered to at least one healthy subject in the form of a chewing gum containing a particulate material containing 4 mg nicotine or an equivalent amount of a pharmaceutically acceptable salt, complex or solvate thereof—results in a plasma concentration of at least about 5 ng/ml such as, e.g., about 6 ng/ml or more, about 7 ng/ml or more, about 8 ng/ml or more, about 9 ng/ml or more or about 10 ng/ml nicotine within at the most about 15 min such as, e.g. within at the most about 10 min, within at the most about 7.5 min, within at the most about 5 min, within at the most about 4 min or within at the most about 3 min after administration.

Dependent on the desired effect, the release of nicotine from a particulate material or from a composition containing the material may be varied. Thus, within the scope of the present invention is also the following embodiments:

A particulate material, which—when administered to at least one healthy subject in the form of a chewing gum containing a particulate material containing 4 mg nicotine or an equivalent amount of a pharmaceutically acceptable salt, complex or solvate thereof— i) results in a plasma concentration of at least about 6 ng/ml nicotine within at the most about 10 min such as, e.g. within at the most about 9 min, at the most about 8 min, at the most about 7 min, at the most about 6 min, at the most about 5 min, at the most about 4 min or at the most about 3 min after administration (e.g. could apply for a relatively fast release composition), ii) results in a plasma concentration of at least about 8 ng/ml nicotine such as, e.g., at least about 10 ng/ml, at least about 12.5 ng/ml, at least about 15 ng/ml or at least about 16 ng/ml within at the most 10 min after administration, iii) results in a plasma concentration of at least about 10 ng/ml nicotine within at the most about 30 min such as, e.g. within at the most about 25 min, within at the most about 20 min, within at the most about 15 min or within at the most about 10 after administration (e.g. could apply for a more extended release composition), iv) results in a plasma concentration of at least about 10 ng/ml nicotine within at the most about 15 min such as, e.g. within at the most about 10 min, within at the most about 7.5 min, within at the most about 5 min, within at the most about 4 min or within at the most about 3 min after administration (e.g. could apply for a medium-fast release composition), v) results in a plasma concentration of at least about 4 ng/ml nicotine such as, e.g., at least about 5 ng/ml, or at least about 6 ng/ml after administration, and/or vi) results in a plasma concentration of at least about 7.5 ng/ml or at least about 10 ng/ml after administration.

Alternatively or complementary, a particulate material according to the invention—when administered to a healty subject in the form of a chewing gum containing a particulate material containing 4 mg nicotine—results in a plasma concentration of at least about 4 ng nicotine such as, e.g., at least about 5 ng, at least about 7.5 ng or at least about 10 ng within at the most 10 min after administration, or for the material that is designed to release nicotine in a faster manner—results in a plasma concentration of at least about 8 ng nicotine such as, e.g., at least about 10 ng, at least about 12.5 ng, at least about 15 ng or at least about 16 ng within at the most 10 min after administration.

The different release may be obtained in different ways. Thus, e.g. coating of the particulate material may be employed in order to obtain a coated particulate material from which the nicotine is released in a slower or delayed manner in order to achieve a prolonged action. A combination of uncoated and coated particulate material may be employed in order to adjust the release profile to a desired release pattern (e.g. not a very fast and not a very slow release) etc. Furthermore, the particulate material can be incorporated into compositions such as, e.g., pharmaceutical compositions and dependent on the specific formulation and formulation technology applied different release patterns can be obtained. In other words, the present invention provides a particulate material that can be formulated to provide fast, medium and slow release of a nicotine, and combinations of such releases.

In accordance with the above, a particulate material or a composition of the invention may be coated so as to delay the release of nicotine or the pharmaceutically acceptable salt, complex or solvate thereof from that part of the material. Suitable coating materials are e.g. film forming polymers such as, e.g., carbomer, carboxymethylcellulose, cellulose acetate, cellulose acetate phthalate, ethylcellulose, hydroxyethyl cellulose, hydroxypropyl cellulose, hydroxypropyl methylcellulose, hydroxypropyl methylcellulose phthalate, methylcellulose, polymethacrylates, polyvinyl alcohol, povidone, shellac, a fatty substance e.g. hard fat, hydrogenated cottonseed oil, hydrogenated vegetable oil, a polyethylene glycol, a polyethylene oxide, a wax, a zein, a sugar or derivatives of sugar e.g. glucose, maltodextrin, polydextrose, sucrose, lactose, alginic acid, carrageenan, sugar alcohols or derivatives of sugar alcohols e.g. mannitol, maltitol, isomalt, xylitol, sorbitol etc.

With respect to a particulate material containing a nicotine salt and MCC (obtained e.g. by using a nicotine salt solution on MCC), the dissolution profile has been found to be somewhat slower in vitro. Thus, the dissolution profiles of nicotine tartrate from a nicotine/MCC particulate material is typically 90% of loaded nicotine released after 5-10 minutes in 1 litre phosphate buffer, pH 7.4 maintained at 37° C. in a dissolution apparatus according to USP, paddle.

The absorption rate is controlled primarily by the release rate from the carrier and pH (amount uncharged nicotine) at the absorptive site. In order to adjust pH at the absorption site, one or more buffer substances may be incorporated into the particulate material or composition of the present invention. The buffer substance may at least partially be sorbed by the MCC. Suitable buffer substances for use in the present context are e.g. alkaline or alkaline earth metal salts such as, e.g., sodium hydroxide, potassium hydroxide, magnesium hydroxyde, carbonates including monocarbonate, bicarbonate and sesquicarbonate such as, e.g, sodium carbonate, sodium hydrogen carbonate, potassium carbonate, potassium hydrogen carbonate, magnesium carbonate, calcium carbonate etc., glycinate, phosphate including monohydrogenphosphate, dihydrogenphosphate and trihydrogenphosphate, glycerophosphate, gluconate, borate, ammonium, and mixtures thereof salts of organic or inorganic acids such as, e.g., acetates, citrates, tartrates etc., In one embodiment, the nicotine or the pharmaceutically acceptable salt, complex or solvate thereof for use in a particulate material or composition according to the invention is selected from nicotine base, nicotine hydrochloride, nicotine dihydrochloride, nicotine tartrate, nicotine bitartrate, nicotine sulfate, nicotine zinc chloride and nicotine salicylate.

To achieve slower release different salts of nicotine is used. Also combinations of the nicotine in its base form and salts can be used to achieve the desired release.

Accordingly, a particulate material or compositon according to the invention may comprise nicotine and one or more pharmaceutically acceptable salts, complexes or solvates thereof. In a specific embodiment a particulate material or a composition according to the invention comprises nicotine and at least one of nicotine tartrate or nicotine bitartrate.

In another aspect, the invention relates to a composition such as, e.g. a pharmaceutical composition comprising a particulate material according to the invention, optionally together with one or more pharmaceutically acceptable excipients. The details and particulars described above with respect to the particulate material applies, whenever relevant, also for a composition of the invention.

The nicotine-containing compositions may be administered to the subject including a human any convenient administration route such as, e.g., oral including the buccal route, nasal, ocular, pulmonary, topical or transdermal route in a dose that is effective for the individual purposes. A person skilled in the art will know how to chose a suitable administration route.

The effective dosage of nicotine may vary depending on the particular nicotine (salt, base etc.) employed, the mode of administration, the condition being treated, the age and condition of the animal to be treated and the severity of the condition being treated. A person skilled in the art can easily ascertain suitable dosages. Normally, in a pharmaceutical composition according to the invention the concentration of nicotine or a pharmaceutically acceptable salt, complex or solvate thereof in the composition is from about 0.5 to about 6 mg calculated as nicotine base.

A pharmaceutical composition according to the invention may be in the form of a solid, semi-solid or fluid dosage form such as, e.g., powders, granules, granulates, dispersions or it may be in the form of a oral suspension, soluble tablet, oral gel, oral powder, granules, cachet, capsule, tablet, controlled release tablet, oral lyophilisate, orodispersible tablet, chewable tablet, oral gum, oromucosal suspension, oromucosal spray, sublingual spray, oromucosal gel, oromucosal paste, medicated chewing gum, gingival gel, gingival paste, gingival patch, oromucosal capsule, sublingual tablet, muco-adhesive buccal tablet, buccal tablet, buccal patch, buccal wafer, lozenge, gel, cutaneous paste, ointment, cutaneous spray, transdermal patch, cutaneous stick, impregnated dressing.

The pharmaceutical compositions may be prepared by any of the method well known to a person skilled in pharmaceutical formulation.

In pharmaceutical compositions, the particulate material is normally combined with a pharmaceutical excipient, i.e. a therapeutically inert substance or carrier.

The carrier may take a wide variety of forms depending on the desired dosage form and administration route.

The pharmaceutically or cosmetically acceptable excipients may be e.g. fillers, binders. disintegrants, diluents, glidants, solvents, emulsifying agents, suspending agents, stabilizers, enhancers, flavours, colors, pH adjusting agents, retarding agents, wetting agents, surface active agents, preservatives etc. Details can be found in pharmaceutical handbooks such as, e.g., Remington's Pharmaceutical Science or Handbook of Pharmaceutical Excipients.

To be more specific, a pharmaceutical composition according to the invention may comprise an additive selected from the group consisting of pH-adjusting agents, stabilizing agents, preservatives, aroma-adjusting agents, flavor-adjusting agents, coloring agents, release-adjusting agents, complexing agents including EDTA. Furthermore, it may contain a buffer substance such as one mentioned herein before.

In those cases where the composition is designed for oral administration including administration to the mouth cavity (e.g. in the form of solid or semi-solid composition such as, e.g., in the form of a chewing gum or lozenge including pastils, toffees, hard boilies and other candy-like compositions) one or more bulk sweeteners may be incorporated in the compositon. Suitable bulk sweeteners are selected from the group consisting of mono-, di-, tri- and polysaccharides, and natural and synthetic non-saccharide-based sweeteners. In specific embodiments, the bulk sweetener is isomalt, xylitol or sorbitol, or combinations thereof.

In other embodiments, a pharmaceutical composition according to the invention may comprise a further therapeutically and/or prophylactically active substance.

A pharmaceutical composition of the invention may also have a further amount of a nicotine incorporated in the composition. Besides the nicotine compounds mentioned above, it may be nicotine cation exchange resin complexes wherein the cation exchanger is selected from the group consisting of methacrylic type containing carboxylic functional groups or polystyrene type either with sulfonic functional groups or phosphonic functional groups.

In a specific embodiment, the particulate material comprised in the composition comprises nicotine base and the futher amount of a nicotine that is incorporated into the composition is selected from the group consisting of nicotine tartrate and nicotine bitartrate.

A pharmaceutical composition according to the invention may also be coated in order to adjust or control the release of nicotine. The coating materials mentioned herein before also applies to the composition. Furthermore, a taste-masking coating may be employed.

In another aspect, the invention relates to the use of a particulate material according to the invention for the preparation of a pharmaceutical composition having a relatively fast onset of nicotine after administration. As mentioned above, the pharmaceutical composition may also be designed to release the nicotine in a more controlled or delayed manner. As described above concerning the particulate material according to the invention, many different release patterns can be obtained dependent on e.g. use of a combination of coated and uncoated particulate material, use of a combination of two or more different nicotines (e.g. free base and salt), use of specific formulation technologies to achieve e.g. a controlled release composition etc. and combinations of these different ways. In the following is described specific embodiments of the invention defined with respect to the release of nicotine of, alternative, with respect to the plasma concentration obtained after administration to a subject.

Thus, in various embodiments the invention relates to a pharmaceutical composition, wherein
i) at least about 50% w/w such as, e.g., at least about 55% w/w, at least about 60% w/w, at least about 65% w/w, at least about 70% w/w or at least about 75% w/w nicotine is released within at the most about 45 min such as, e.g., at the most about 30 min after oral administration (e.g. fast, medium fast release),
ii) at least about 50% w/w such as, e.g., at least about 55% w/w, at least about 60% w/w, at least about 65% w/w, at least about 70% w/w or at least about 75% w/w nicotine is released within at the most about 45 min such as, e.g., at the most about 30 min determined in an in vitro dissolution test according to Ph.Eur (e.g. fast, medium fast release),
iii) at the most about 60% w/w such as, e.g., at the most about 55% w/w, at the most about 50% w/w, at the most about 45%, at the most about 40%, at the most about 35% w/w or at the most about 30% w/w nicotine is released within at the most about 45 min such as, e.g., at the most about 30 min after oral administration (e.g. medium slow, slow release),
iv) at at the most about 60% w/w such as, e.g., at the most about 55% w/w, at the most about 50% w/w, at the most about 45%, at the most about 40%, at the most about 35% w/w or at the most about 30% w/w nicotine is released within at the most about 45 min such as, e.g., at the most about 30 min determined in an in vitro dissolution test according to Ph.Eur (e.g. medium slow, slow release), With respect to the effect obtained after administration of a composition according to the invention a suitable plasma concentration of nicotine must be obtained within a suitable period of time. Accordingly, the invention relates to a pharmaceutical composition, which—when administered to at least one healthy subject in an amount corresponding to 4 mg nicotine or an equivalent amount of a pharmaceutically acceptable salt, complex or solvate thereof
i) results in a plasma concentration of at least about 5 ng/ml such as, e.g., about 6 ng/ml or more, about 7 ng/ml or more, about 8 ng/ml or more, about 9 ng/ml or more or about 10 ng/ml or more of nicotine within at the most about 30 min such as, e.g. within at the most about 25 min, within at the most about 20 min, within at the most about 15 min or within at the most about 10 after administration (e.g. relatively fast to medium fast release and fast to medium fast onset of action),
ii) results in a plasma concentration of at least about 5 ng/ml such as, e.g., about 6 ng/ml or more, about 7 ng/ml or more, about 8 ng/ml or more, about 9 ng/ml or more or about 10 ng/ml nicotine within at the most about 15 min such as, e.g. within at the most about 10 min, within at the most about 7.5 min, within at the most about 5 min, within at the most about 4 min or within at the most about 3 min after administration (e.g. relatively fast to medium fast release and fast to medium fast onset of action),
iii) results in a plasma concentration of at least about 6 ng/ml nicotine within at the most about 10 min such as, e.g. within at the most about 9 min, at the most about 8 min, at the most about 7 min, at the most about 6 min, at the most about 5 min, at the most about 4 min or at the most about 3 min after administration (e.g. fast release, fast onset of action),
iv) results in a plasma concentration of at least about 8 ng/ml nicotine such as, e.g., at least about 10 ng/ml, at least about 12.5 ng/ml, at least about 15 ng/ml or at least about 16 ng/ml within at the most about 10 min after administration (e.g. relatively fast release and fast onset of action).
v) results in a plasma concentration of at least about 4 ng/ml nicotine such as, e.g., at least about 5 ng/ml, or at least about 6 ng/ml after administration, and/or
vi) results in a plasma concentration of at least about 7.5 ng/ml or at least about 10 ng/ml after administration.

As it appears from the above, the release of nicotine can be adjusted to a desired situation. Thus, the composition may be designed to release nicotine relatively fast to obtain an enhanced onset of action or it may be designed to release nicotine in an extended manner to obtain a prolonged effect. Furthermore it may be designed to release at least a part of the nicotine contained in the composition in a fast manner to obtain an enhanced onset of action and the remaining part of the nicotine in an extended manner to obtain a prolonged action. In the latter case, the plasma concentration of nicotine after oral administration shows a mono-, bi- or multiphasic curve.

In a specific embodiment, a composition is in the form of a chewing gum.

Manufacturing of chewing gum as well as suitable excipients and additve for use in chewing gums are well-known to a person skilled in the art (see e.g. WO 03/084338 including references cited therein; these references are hereby included by reference). Accordingly, the gum bases may be of any conventional nature known in the art such as, e.g., a gum base of natural or synthetic origin available from a commercial source. Natural gum bases include e.g. chicle, jelutong gum, lechi de caspi gum, soh gum, siak gum, katiau gum, sorwa gum, balata gum, pendare gum, malaya gum and peach gum, natural cauchouc and natural resins such as dammar and mastix. Synthetic gum bases include elastomers (polymers, masticating substances). Normally, additives like plasticizers, fillers (e.g. texturizers), softeners (e.g. fats or waxes), sweeteners, mouth-feel improving agents and/or emulsifiers are added.

In a still further aspect, the invention relates to a method for treating a nicotine-related disorder of a subject, the method comprising administering a sufficient amount of nicotine or a pharmaceutically acceptable salt, complex or solvate thereof in a particulate material or in a pharmaceutical composition according to the invention to the subject in need thereof.

More specifically, the nicotine-related disorder mentioned above may be tobacco dependence, Parkinsons disease, ulcerative colitis, Alzheimers disease, schizophrenia, ADHD (Attention Deficit Hyperactivity Disorder), Tourette's syndrome, ulcerous colitis and post-smoking-cessation weight control.

The details and description relating to the particulate material aspect apply mutatis mutandis to the other aspects of the invention.

The invention is further illustrated in the following non-limiting examples and in the figures, wherein.

EXAMPLES

Loading Nicotine on MCC

Nicotine base is dissolved in ethanol to a concentration of 0.1-8% (w/w) calculated on the dried adduct, and added on MCC in a high shear mixer equipped with vacuum drying or equivalent equipment. After a mixing/distribution step the powder is dried and the nicotine concentration determined by HPLC. The in vitro release is determined using a standard dissolution apparatus described in USP (paddle) and HPLC. Salts of nicotine e.g. nicotine tartrate, is dissolved in a water/ethanol mixture and processed as described above.

The drying process is of importance since a too effective drying; high vacuum and/or temperature will negatively influence the stability and content of the added nicotine. The dried nicotine/MCC particulate material is stable for up to 14 weeks stored openly at 40° C. and 50% relative humidity (RH) and for over 14 weeks stored openly at 20° C. and 55% RH.

Stability

Stability has been determined for nicotine/MCC particulate materials with a nicotine concentration of 1% (w/w). The dried powder has been stored openly in a thin layer at 20° C./55% RH and 40° C./50% RH.

TABLE 1

Stability of nicotine/MCC particulate materials, 1% nicotine (w/w) stored openly, i.e. distributed in thin layer in a petri dish, at 20° C./55% RH and 40° C./50% RH

| | | | Concentration of nicotine, (mg/g). | |
|---|---|---|---|---|
| MCC quality | Nicotine | Start values | 40° C./ 50% RH | 20° C./ 55% RH |
| Avicel PH-102 | Tartrate | 9.5 | 10.1$^8$ | 9.3$^{14}$ |
| Avicel PH-102 | Base | 10.8 | 8.9$^{14}$ | 9.8$^{14}$ |
| Avicel PH-200 | Base | 10.6 | 10.9$^8$, 10.7$^{14}$, 11.0$^{22}$ | 11.8$^{14}$, 10.9$^{22}$ |

$^8$ = analysed after 6 weeks
$^{14}$ = analysed after 14 weeks and
$^{22}$ = analysed after 22 weeks.

No discoloration of the product and no increase in non-nicotine peaks in the chromatograms where observed, indicating a stable product over the period investigated.

Load Ratio

The load ratio has been determined for nicotine/MCC particulate materials with a starting nicotine concentration of approx. 12% (w/w). The dried powder has been stored openly in a thin layer at 20° C. 55% RH and 40° C./50% RH.

TABLE 2

Load ratio of nicotine base/MCC particulate materials, initially loaded with approx. 12% nicotine (w/w) stored openly, i.e. distributed in thin in a petri dish, at 40° C./50% PH

| | Concentration of nicotine, (% (w/w)). | | | |
|---|---|---|---|---|
| MCC quality | Start values | 2 weeks | 4 weeks | 6 weeks |
| Vivacel 12 | 11.7 | 8.2 | 7.7 | 7.6 |
| Avicel PH-301 | 12.4 | 8.3 | 8.2 | 7.8 |
| Avicel PH-102 | 12.1 | 8.4 | 8.0 | 7.8 |
| Avicel PH-200 | 12.2 | 8.6 | 8.2 | 7.9 |

The results shows that a load ratio of approx. 8% (w/w) of nicotine base can be used with maintained good stability properties on the different MCC qualities. Above 8% (w/w) the MCC (in the employed qualities) seems to be over-saturated with nicotine. The first steep loss of nicotine is most probably due to a over-saturation of the pores' content of nicotine; the excess nicotine will most likely evaporate quickly from the particulate material.

In vitro Release

The release in vitro can be varied depending on origin of nicotine, i.e. base and salt form. The release is rapid for all tested combinations and generally more so when the base is used.

With the use of coating on the dried nicotine/MCC particulate material more prolonged release profiles could be achieved. A slight retardation in the release profile was achieved with the use of approx. 50% (w/w) polyethylene glycole (PEG) 8000. A more retarded release profile was achieved by the use of approx. 50% (w/w) hydrogenated cottonseed oil (Akofine E).

TABLE 3

In vitro release of nicotine/MCC particulate materials in 37° C. phosphate buffer, pH 7.4 in USP dissolution apparatus. Steady state concentration is used for calculations.

| | | Nicotine concentration in % of steady state conc. | | | |
|---|---|---|---|---|---|
| MCC quality | Nicotine | After 1 min | After 2 min | After 5 min | After 10 min |
| Vivacel 12 | Base | 89.4 | 92.1 | 95.4 | 96.2 |
| Vivacel 12 | Tartrate | 70.5 | 74.6 | 90.2 | 98.7 |
| Avicel PH-105 | Tartrate | 73.8 | 75.0 | 82.9 | 92.6 |
| Avicel PH-200 | Base | 100.3 | 99.8 | 99.0 | 99.7 |
| Avicel PH-101 | Base | 96.5 | 98.3 | 97.3 | 97.2 |
| Avicel PH-102 | Base | 98.4 | 99.1 | 99.8 | 99.5 |
| Avicel PH-102$^1$ | Base | 85.5 | 90.4 | 95.2 | 98.8 |
| Avicel PH-102$^2$ | Base | 73.3 | 77.1 | 83.5 | 90.4 |
| Avicel PH-102$^3$ | Base | 37.8 | 50.0 | 63.3 | 73.0 |

$^1$The dried adduct was coated with 50% (w/w) PEG 8000.
$^2$The dried adduct was coated with 50% (w/w) hydrogenated cottonseed oil (Akofine E).
$^3$The dried adduct was coated with 60% (w/w) hard fat (mixture of Witepsol E-76 and E-85 in a 1:1 ratio).

In vivo Plasma Nicotine

Figure 2:
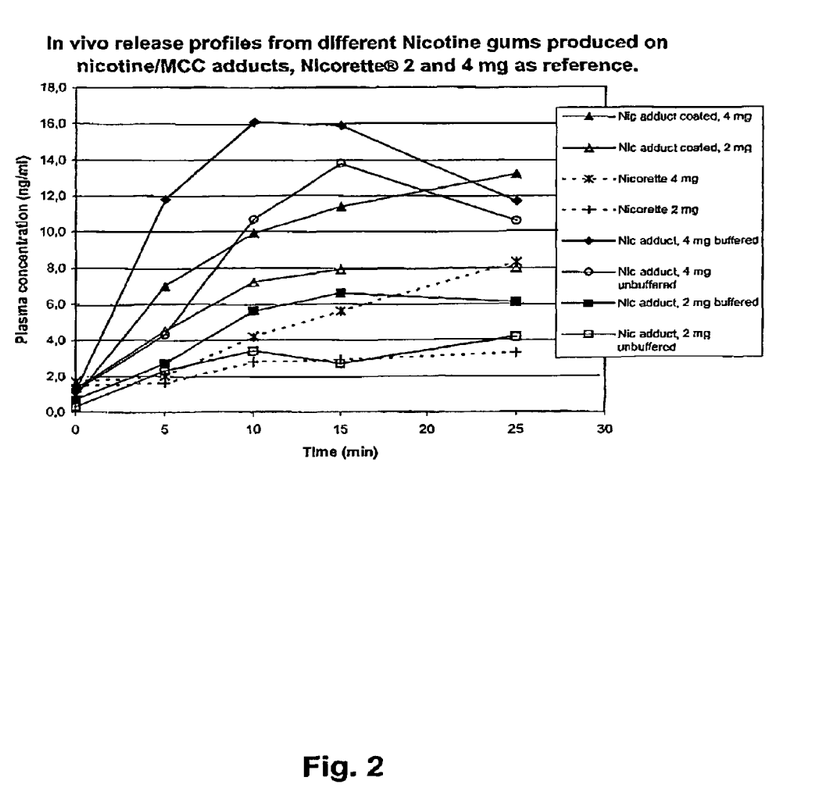
FIG. 2 shows the plasma concentration versus time profile of nicotine from compositions according to the invention compared with commercially available products.

Nicotine/MCC particulate material, 4-5% (w/w) was incorporated in a chewing gum composition to final concentrations of 2 and 4 mg nicotine/gum. The gums were produced using direct compression and analysed for initial nicotine content. The gums were chewed by the same test person and blood samples were retrieved prior chewing and after 5, 10, 15 and 20 minutes. The blood samples were analysed for nicotine and cotinine. The human in vivo plasma profiles demonstrate that the desired profiles could be achieved with good margin with the use of the nicotine/MCC particulate material in one formulation type, chewing gum. Other products like tablets, lozenges, gels, suspensions, sprays, patches etc may also be used with proper formulation strategies. In FIG. 2 is shown the results of the in vivo study.

The production process is a conventional process utilising standard equipment for pharmaceutical manufacturing. Nicotine is incorporated in MCC. Nicotine base is pre-added to the granulation liquid, ethanol, 99.5% and added to MCC in a vacuum high shear mixer i.e. Zanchetta Rotolab, or equivalent. The wet mass is dried under vacuum in the mixer. Drying on trays could be an alternative.

The gum powder is passed through a 1 mm sieve to ensure that no lumps remain from the transportation. The gum powder and the nicotine-incorporated MCC is mixed with all other excipients except magnesium stearate in an ordinary mixer, double cone mixer or equivalent. In a second mixing step magnesium stearate is admixed. Thereafter DC chewing gums of 1.25 g are compressed in an ordinary rotary tablet press equipped with diameter 17 mm concave punches.

| Composition of 2 mg chewing gum tablet core | | |
| --- | --- | --- |
| Ingredient | Quantity (mg/unit) | Function |
| Nicotine base* | 2.00 | Active ingredient |
| Gum Powder | 1000 | Gum base |
| Isomalt, DC 100 | 134 | Filling agent, sweetener |
| Microcrystalline cellulose, type PH-102 | 61.0 | Nicotine carrier |
| Talc | 37.5 | Antiadherent |
| Magnesium stearate | 12.5 | Lubricant |
| Silica, colloidal anhydrous, Aerosil 200 | 2.00 | Glidant |
| Acesulfame potassium | 0.625 | Sweetener |
| Ethanol 99.5% (w/w)* | — | Granulation liquid |
| Target Weight | 1 250 | |
| Composition of the coating solution | | |
| Ingredient | Amount (%) | Function |
| Isomalt, GS | 65.00 | Coating sugar |
| Purified water | 29.80 | Solvent |
| Gum arabicum, 50% | 4.10 | Binder |
| Titan dioxide | 1.00 | Coloring agent |
| Aspartame | 0.05 | Sweetener |
| Acesulfame potassium | 0.05 | Sweetener |
| Target Amount | 100 | |

The compressed gum cores can be coated in an ordinary rotating coating pan with the coating solution described above to an target end weight of 1600 mg. The final polishing is done with carnauba wax.

| Composition of 4 mg chewing gum tablet core | | |
| --- | --- | --- |
| Ingredient | Quantity (mg/unit) | Function |
| Nicotine base* | 4.00 | Active ingredient |
| Gum Powder | 1000 | Gum base |
| Isomalt, DC 100 | 125 | Filling agent, sweetener |
| Microcrystalline cellulose, type PH-102 | 70.0 | Nicotine carrier |
| Talc | 37.5 | Antiadherent |
| Magnesium stearate | 12.5 | Lubricant |
| Silica, colloidal anhydrous, Aerosil 200 | 2.00 | Glidant |
| Acesulfame potassium | 0.625 | Sweetener |
| Ethanol 99.5% (w/w)* | — | Granulation liquid |
| Target Weight | 1 250 | |

All documents mentioned herein are incorporated herein by reference in their entirety.

The invention claimed is:

1. A pharmaceutically acceptable, nicotine-containing, particulate material for relatively fast release of the nicotine upon contact with a human subject, the material comprising a combination of:
   a) a particulate microcrystalline excipient having suitable porous structure and bulk density for allowing nicotine to sorb in the porous structure of the excipient upon contact; and
   b) at least 0.5 milligrams of nicotine sorbed within the porous structure, the particulate material having a concentration of nicotine of 0.1 to 8% (w/w), and wherein the nicotine sorbed within the porous structure is chemically and/or physically stable for at least 22 weeks when stored at a temperature of 40° C. and a relative humidity of 50%.

2. The material of claim 1, where the excipient comprises microcrystalline cellulose.

3. The material of claim 1, wherein the nicotine is adsorbed to the particulate excipient.

4. The material of claim 1, wherein the nicotine is contained in the particulate excipient.

5. The material of claim 1, wherein said nicotine is selected from the group consisting of nicotine, nicotine derivatives, salts of nicotine, complexes of nicotine, solvates of nicotine, salts of nicotine derivatives, complexes of nicotine derivatives or solvates of nicotine derivatives.

6. The material of claim 5, wherein the nicotine is selected from the group consisting of nicotine or nicotine derivative base, nicotine or nicotine derivative hydrochloride, nicotine or nicotine derivative dihydrochloride, nicotine or nicotine derivative monotartrate, nicotine or nicotine derivative bitartrate, nicotine or nicotine derivative sulfate, nicotine or nicotine derivative zinc chloride monohydrate, nicotine or nicotine derivative salicylate, and wherein nicotine is present as racemate or in the form of any of its enantiomers or mixtures thereof.

7. The material of claim 1, wherein at least 90% w/w of the nicotine in said particulate excipient is released when said excipient is placed in 1 liter of phosphate buffer at pH 7.4, at 37° C., for 30 minutes in a dissolution apparatus of USP, paddle.

8. The material of claim 1, wherein at least 90% w/w of the nicotine in said particulate excipient is released when said excipient is placed in 1 liter of phosphate buffer at pH 7.4, at 37° C., for 20 minutes in a dissolution apparatus of USP, paddle.

9. The material of claim 1, wherein the concentration of nicotine is at or less than 7.5% w/w.

10. The material of claim 1, wherein the excipient is incorporated into a chewing gum.

11. The material of claim 10, wherein the nicotine in the excipient is present in an amount of about 4 mg.

12. The material of claim 10, wherein the chewing gum composition is capable of delivering nicotine to a human subject chewing said gum, such that the concentration of nicotine in the subject's blood plasma is about 4 ng/ml or greater upon chewing the gum.

13. The material of claim 12, wherein the plasma concentration of nicotine of about 4 ng/ml or greater is reached within about 10 minutes or less of the subject chewing the gum.

14. The material of claim 10, wherein the chewing gum composition is capable of delivering nicotine to a human subject chewing said gum, such that the concentration of nicotine in the subject's blood plasma is about 5 ng/ml or greater upon chewing the gum.

15. The material of claim 10, wherein the chewing gum composition is capable of delivering nicotine to a human subject chewing said gum, such that the concentration of nicotine in the subject's blood plasma is about 6 ng/ml or greater upon chewing the gum.

16. The material of claim 10, wherein the chewing gum composition is capable of delivering nicotine to a human subject chewing said gum, such that the concentration of nicotine in the subject's blood plasma is about 7.5 ng/ml or greater upon chewing the gum.

17. The material of claim 10, wherein the chewing gum composition is capable of delivering nicotine to a human subject chewing said gum, such that the concentration of nicotine in the subject's blood plasma is about 8 ng/ml or greater upon chewing the gum.

18. The material of claim 1, wherein at least part of the excipient is coated with a material that delays the release of nicotine from the particulate material.

19. The material of claim 18, wherein at least part of the excipient is coated with a film-forming polymer selected from the group consisting of carbomer, carboxymethylcellulose, cellulose acetate, cellulose acetate phthalate, ethylcellulose, hydroxyethyl cellulose, hydroxypropyl cellulose, hydroxypropyl methylcellulose, hydroxypropyl methylcellulose phthalate, methylcellulose, polymethacrylates, polyvinyl alcohol, povidone, shellac, a fatty substance selected from the group consisting of hard fat, hydrogenated cottonseed oil, and hydrogenated vegetable oil, a polyethylene glycol, a polyethylene oxide, a wax, a zein, a sugar or derivatives of sugar selected from the group consisting of glucose, maltodextrin, polydextrose, lactose, alginic acid, carrageenan, and sugar alcohols or derivatives of sugar alcohols selected from the group consisting of mannitol, maltitol, isomalt, xylitol, and sorbitol.

20. The material of claim 1, wherein the nicotine in the particulate material comprises nicotine base.

21. The material of claim 1, further comprising a buffer substance.

22. The material of claim 21, wherein the buffer substance is at least partially sorbed by the excipient.

23. The material of claim 21, wherein the buffer substance is selected from the group consisting of a carbonate, glycinate, phosphate, glycerophosphate, acetate, gluconate, citrate, borate, ammonium, and mixtures thereof.

24. The material of claim 1, wherein about 50% w/w or more of nicotine is released within about 30 minutes or less as determined by the in vitro dissolution test of Ph. Eur.

25. The material of claim 1, wherein about 55% w/w or more of nicotine is released within about 30 minutes or less as determined by the in vitro dissolution test of Ph. Eur.

26. The material of claim 1, wherein about 60% w/w or more of nicotine is released within about 30 minutes or less as determined by the in vitro dissolution test of Ph. Eur.

27. The material of claim 1, wherein about 65% w/w or more of nicotine is released within about 30 minutes or less as determined by the in vitro dissolution test of Ph. Eur.

28. The material of claim 1, wherein about 70% w/w or more of nicotine is released within about 30 minutes or less as determined by the in vitro dissolution test of Ph. Eur.

29. The material of claim 1, wherein about 50% w/w or more of nicotine is released within about 45 minutes or less as determined by the in vitro dissolution test of Ph. Eur.

30. The material of claim 1, wherein about 55% w/w or more of nicotine is released within about 45 minutes or less as determined by the in vitro dissolution test of Ph. Eur.

31. The material of claim 1, wherein about 60% w/w or more of nicotine is released within about 45 minutes or less as determined by the in vitro dissolution test of Ph. Eur.

32. The material of claim 1, wherein about 65% w/w or more of nicotine is released within about 45 minutes or less as determined by the in vitro dissolution test of Ph. Eur.

33. The material of claim 1, wherein about 70% w/w or more of nicotine is released within about 45 minutes or less as determined by the in vitro dissolution test of Ph. Eur.

34. The material of claim 1, and further including a pharmaceutically acceptable carrier comprising one or more pharmaceutically acceptable excipients.

35. The material of claim 1, wherein the concentration of nicotine is from about 0.5 mg to about 6 mg calculated as nicotine base.

36. The material of claim 1, wherein the material is in the form of a solid, semi-solid, or fluid dosage form.

37. The material of claim 1, wherein the material is in the form of an oral suspension, a soluble tablet, an oral gel, an oral powder, granules, a sachet, a capsule, a tablet, a controlled release tablet, an oral lyophilisate, an orodispersible tablet, a chewable tablet, an oral gum, an oromucosal suspension, an oromucosal spray, a sublingual spray, an oromucosal gel, an oromucosal paste, chewing gum, gingival gel, gingival patch, oromucosal capsule, sublingual tablet, muco-adhesive buccal tablet, buccal tablet, buccal patch, buccal wafer, lozenge, gel, cutaneous paste, ointment, cutaneous spray, transdermal patch, cutaneous stick, or an impregnated dressing.

38. The material of claim 1, further comprising an additive selected from the group consisting of pH-adjusting agents, stabilizing agents, preservatives, aroma-adjusting agents, flavor-adjusting agents, coloring agents, release-adjusting agents, and complexing agents.

39. The material of claim 1, further comprising one or more bulk sweeteners selected from the group consisting of mono-, di-, tri- and polysaccharides, natural and synthetic non-saccharide-based sweeteners, isomalt, xylitol, and sorbitol or combinations thereof.

40. The material of claim 1, in a solid or semi-solid form for oral application.

41. The material of claim 40, wherein the material is in the form of chewing gum, lozenge, and other candy-like compositions.

42. The material of claim 40, further comprising an additional active substance, in addition to the nicotine-containing excipient.

43. The material of claim 40, wherein an additional amount of nicotine is added to the material.

44. A method for treating a nicotine-related disorder of a human subject, the method comprising administering an effective amount of nicotine from the particulate excipient as defined in claim 1 to the subject.

45. The method of claim 44, wherein the administration is to treat tobacco dependence, Parkinson's disease, ulcerative colitis, Alzheimer's disease, schizophrenia, ADHD, Tourett's syndrome, and post-smoking weight gain.

46. A dosage form comprising a pharmaceutically acceptable, nicotine-containing, particulate material for relatively fast release of the nicotine upon contact with a human subject, the material comprising a combination of:
   a) a particulate microcrystalline excipient having suitable porous structure and bulk density for allowing nicotine to sorb in the porous structure of the excipient upon contact; and
   b) nicotine sorbed in the porous structure in a concentration of 0.1 to 8% (w/w),
   wherein the amount of particulate material contained in the dosage form corresponds to an effective amount of nicotine of from 0.5 to 6 mg nicotine and wherein the nicotine sorbed within the porous structure is chemically and/or physically stable for at least 22 weeks when stored at a temperature of 40° C. and a relative humidity of 50%.

47. The dosage form of claim 46 selected from the group consisting of an oral suspension, a soluble tablet, an oral gel, an oral powder, granules, a sachet, a capsule, a tablet, a controlled release tablet, an oral lyophilisate, an orodispersible tablet, a chewable tablet, an oral gum, an oromucosal suspension, an oromucosal spray, a sublingual spray, an oromucosal gel, an oromucosal paste, a medicated chewing gum, a gingival gel, a gingival paste, a gingival patch, an oromucosal capsule, a sublingual tablet, a muco-adhesive buccal tablet, a buccal tablet, a buccal patch, a buccal wafer, a lozenge, a gel, a cutaneous paste, an ointment, a cutaneous spray, a transdermal patch, a cutaneous stick, and an impregnated dressing.

48. A pharmaceutically acceptable, nicotine-containing, composition comprising a particulate microcrystalline excipient material for relatively fast release of the nicotine upon contact with a human subject, the particulate microcrystalline excipient material comprising a combination of:
   i) a particulate microcrystalline excipient having a suitable porous structure and bulk density for allowing nicotine to sorb in the porous structure of the excipient upon contact; and
   ii) at least 0.5 mg of nicotine sorbed within the porous structure, and wherein the nicotine is sorbed within the porous structure of the particulate microcrystalline excipient at a concentration of 0.1 to 8% (w/w) and wherein the nicotine sorbed within the porous structure is chemically and/or physically stable for at least 22 weeks when stored at a temperature of 40° C. and a relative humidity of 50%.

49. The material of claim 1, wherein the nicotine sorbed within the porous structure consists of 0.5 to 6 mg nicotine base or an equivalent amount of a pharmaceutically acceptable salt, complex or solvate thereof.

50. The material of claim 1, wherein the nicotine sorbed within the porous structure consists of 2 to 4 mg nicotine base or an equivalent amount of a pharmaceutically acceptable salt, complex or solvate thereof.

51. The material of claim 1, wherein the porous structure of the particulate microcrystalline excipient is saturated with nicotine.

52. The material of claim 1, wherein at least about $2/3$ of the total nicotine present in the composition is sorbed within the porous structure of the particulate microcrystalline excipient.

53. The material of claim 1, wherein the nicotine is sorbed within the porous structure by introducing nicotine dissolved in a hydrophilic solvent into the porous structure.

54. A pharmaceutically acceptable, nicotine-containing, particulate material for relatively fast release of the nicotine upon contact with a human subject, the material comprising a combination of:
   a) a particulate crystalline excipient having suitable porous structure and bulk density for allowing nicotine to sorb in the porous structure of the excipient upon contact; and
   b) a nicotine compound sorbed within the porous structure, wherein the nicotine compound is nicotine or a pharmaceutically acceptable salt, complex or solvate thereof, and wherein at least 90% w/w of the nicotine compound in said particulate excipient is released when said excipient is placed in 1 liter of phosphate buffer at pH 7.4, at 37° C., for 30 minutes in a dissolution apparatus of USP, paddle.

55. The material of claim 54, wherein the nicotine is sorbed within the porous structure by introducing nicotine dissolved in a hydrophilic solvent into the porous structure.

56. The material of claim 54, wherein the particulate crystalline excipient comprises a crystalline cellulose material.

* * * * *